United States Patent
Roques et al.

(10) Patent No.: US 7,120,173 B2
(45) Date of Patent: Oct. 10, 2006

(54) METHOD FOR ILLUMINATING PARTICLES FOR THE PURPOSE OF FORMING THEIR IMAGES

(75) Inventors: Sandrine Roques, Tournefeuille (FR); Christian Lopez, Le Castera (FR)

(73) Assignee: Airbus France, Toulouse (FR)

( * ) Notice: Subject to any disclaimer, the term of this patent is extended or adjusted under 35 U.S.C. 154(b) by 245 days.

(21) Appl. No.: 10/868,037

(22) Filed: Jun. 16, 2004

(65) Prior Publication Data
US 2004/0257450 A1 Dec. 23, 2004

(30) Foreign Application Priority Data
Jun. 20, 2003 (FR) ................................... 03 07463

(51) Int. Cl.
*H01S 3/30* (2006.01)
*G01N 15/02* (2006.01)
(52) U.S. Cl. .......................................... 372/3; 356/336
(58) Field of Classification Search .................... 372/3; 356/336
See application file for complete search history.

(56) References Cited
U.S. PATENT DOCUMENTS

| 5,530,551 | A  | * | 6/1996  | Cantrall et al. ............. 356/394 |
| 6,301,271 | B1 |   | 10/2001 | Sanders et al. |
| 6,567,430 | B1 | * | 5/2003  | Islam et al. ..................... 372/3 |
| 6,567,605 | B1 |   | 5/2003  | Rice et al. |
| 6,885,683 | B1 | * | 4/2005  | Fermann et al. .............. 372/25 |
| 2002/0159060 | A1 |   | 10/2002 | Roques et al. |
| 2004/0213300 | A1 | * | 10/2004 | Cook ........................... 372/3 |

FOREIGN PATENT DOCUMENTS

EP 1183518 3/2002

OTHER PUBLICATIONS

Saha S K: "Fiber Amplifier: CS/sub 2/Filled Fiber Used as a Ramen Amplifier," Database Accession No. 5763894 XP002269303, Institute of Electrical Engineers, vol. 25, No. 4, pp. 255-260, Oct.-Dec. 1996.
Patent Abstracts of Japan, vol. 013, No. 057, Feb. 9, 1989.
Preliminary Search Report dated Feb. 5, 2004.

* cited by examiner

*Primary Examiner*—Minsun Harvey
*Assistant Examiner*—Marcia A. Golub
(74) *Attorney, Agent, or Firm*—Stevens, Davis, Miller & Mosher, LLP

(57) ABSTRACT

Peak power of a coherent light beam generated by a laser and injected into an optical fiber is chosen so that the spectrum of the light beam emanating from the fiber, for illuminating particles, includes Raman lines.

6 Claims, 2 Drawing Sheets

METHOD FOR ILLUMINATING PARTICLES FOR THE PURPOSE OF FORMING THEIR IMAGES

FIELD OF THE INVENTION

The present invention relates to a method for illuminating particles for the purpose of forming their images. The method of the present invention is particularly, although not exclusively, suitable for particle size analysis of particles of all kinds, and in particular water droplets.

BACKGROUND OF RELATED ART

A method of this type is already known, for example from document EP-1 183 518, in which a coherent light beam, preferably a pulsed light beam, is injected into an optical fiber, via one end of the fiber, and said particles are illuminated by the pulses of the light beam emanating from the other end of said fiber.

To implement such a method, a monomode optical fiber is chosen for the purpose of preventing the occurrence of parasitic noise in said images.

However, to obtain contrasted sharp images of said particles, the energy injected at each pulse of the coherent light beam must be high enough to allow said particles to be illuminated sufficiently to form their images. In such a case when the injected light energy is high, despite the use of a monomode optical fiber, the images of said particles exhibit parasitic background noise and a moiré effect that degrade their sharpness.

SUMMARY OF THE INVENTION

The object of the present invention is to remedy these drawbacks.

For this purpose, according to the invention, the method for illuminating particles for the purpose of forming their images, in which method a coherent light beam is injected into the core of a monomode optical fiber, at one end of said fiber, and said particles are illuminated by the light beam emanating from said core at the other end of said monomode optical fiber, is noteworthy due to the fact that the peak power of said injected coherent light beam is chosen so that the spectrum of said emanating light beam has, alongside the wavelength of said injected coherent light beam, lines of shifted wavelengths generated by Raman conversion in the material of said core.

Specifically, the Applicant has found that, surprisingly and unexpectedly, and taking the contrary standpoint of a person skilled in the art, who by technical reflex tends to preserve, by any means, the single frequency of the illumination light beam, it is possible to remove, from said images, the background noise and the moiré effect by delivering sufficient energy into the optical fiber to cause Raman conversion of the light beam while it propagates along said monomode optical fiber.

One a posteriori explanation of this beneficial effect of the Raman lines could be the following:

impurities are present in the optics of the device for illuminating the particles and of the camera for taking images of the latter, so that, when these impurities are illuminated by a high-energy coherent laser beam, they cause diffraction phenomena with the appearance of interference effects, which results in a background noise. In addition, the reflections off the various optics cause interference fringes, which are manifested by a moiré effect in the images; and however, when the illumination beam is no longer a single-frequency beam but, on the contrary, includes Raman lines, the various diffraction signals from said impurities resulting from the various Raman wavelengths mix together and counteract one another, so that the sharpness of the particles is improved.

Of course, the above explanation is merely a hypothesis, any invalidation of which would not prejudice the present invention.

As is known, the first Raman line is caused by the action of said coherent light beam on the material of the core of the optical fiber and has a wavelength greater than that of said beam. Likewise, the second Raman line is caused by the action of the first Raman line on the material of the core of the optical fiber and has a wavelength greater than that of said first Raman line, etc., an nth Raman line being caused by the action of the (n−1)th Raman line on the material of said core and having a wavelength greater than that of said (n−1)th Raman line (n being an integer).

Thus, the wavelength of the Raman lines progressively increases. To avoid the inconvenience due to the increase in Airy spots on the images of said particles and, therefore, to prevent the quality of said images being degraded, it is advantageous to take measures to ensure that, in said light beam emanating from said monomode optical fiber, there is no Raman line in the infrared or close to the infrared. This may be achieved by choosing the length of said monomode optical fiber appropriately.

To implement the method according to the present invention, it is advantageous to use a known monomode optical fiber having a specific wavelength, that is to say a monomode optical fiber in which the diameter of the core is matched to the wavelength of the beam to be transmitted by the optical fiber and is an increasing function of said wavelength. For example, such a monomode optical fiber matched to a wavelength of 515 nm may have a core diameter of 3 µm, whereas another one, matched to a wavelength of 780 nm, may have a core diameter of 4.9 µm.

With such monomode optical fibers with specific wavelengths, another feature of the present invention is that said injected coherent light beam, having a wavelength of $\lambda_1$, is injected into the core of a monomode optical fiber having a specific wavelength matched to a wavelength $\lambda_2$ of greater than $\lambda_1$.

Thus, the area for injection of the coherent light beam into said core may be increased and the power density per unit area injected at the input of the optical fiber may be high enough, but without saturating the latter.

Of course, measures must be taken to ensure that, by using a core diameter larger than that matched to the wavelength $\lambda_1$, the propagation within the fiber remains monomode. This is generally satisfied when the $\lambda_2/\lambda_1$ ratio is at least approximately equal to 1.2.

In one particular way of implementing the method according to the invention, $\lambda_1$ is equal to 532 nm and $\lambda_2$ is equal to 630 nm.

BRIEF DESCRIPTION OF THE DRAWINGS

The figures of the appended drawing will make it clearly understood how the invention can be realized. In these figures, identical references denote similar elements.

DETAILED DESCRIPTION OF THE INVENTION

Figure 1:
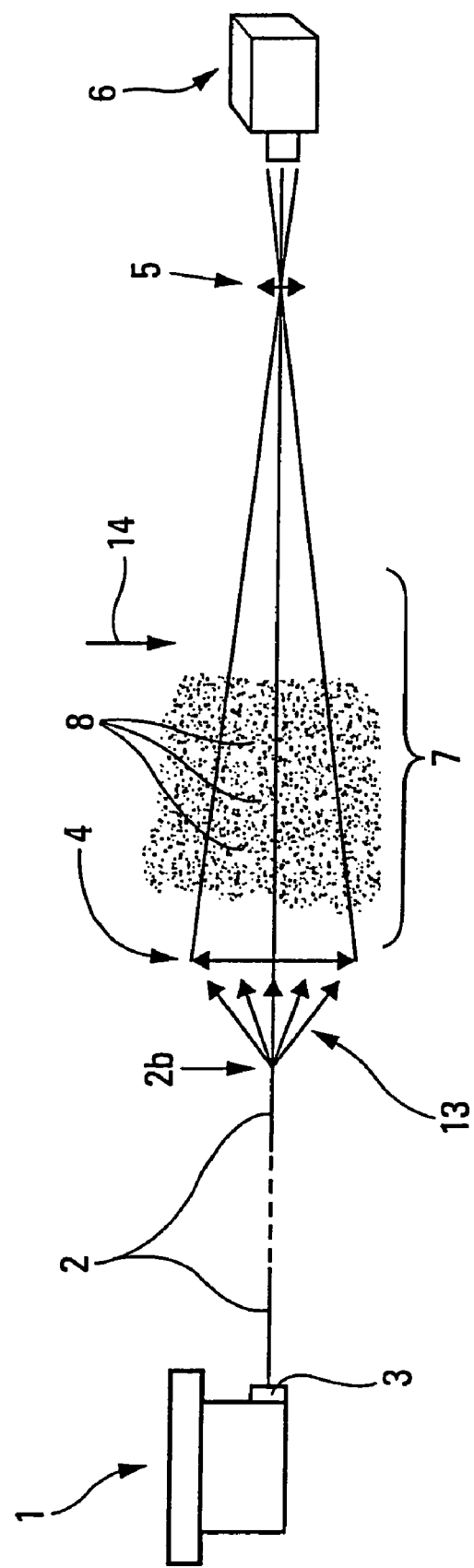
FIG. 1 shows schematically a particle size analyzer employing the method according to the present invention.

The analyzer illustrated schematically in FIG. 1 comprises a pulsed laser 1, coupled to one end 2a of an optical fiber 2 by means of a coupler 3. The other end 2b of the optical fiber 2 illuminates a field optic 4 that focuses the light beam emerging from the optical fiber 2 onto the objective optic 5 of a camera 6, defining a measurement region 7 in which particles 8 lie.

Said particles 8 may be stationary or passing through, possibly at high speed, the measurement region 7, as is shown symbolically in FIG. 1 by the arrow 14.

Figure 3:
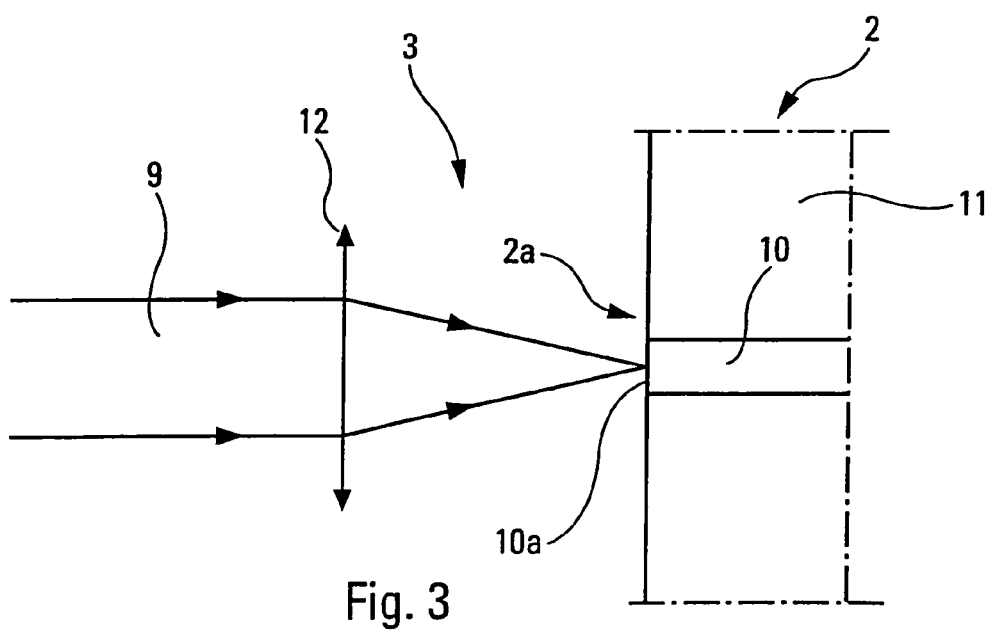
FIG. 3 shows schematically the injection of the coherent light beam into the core of said optical fiber.

The laser 1 is, for example, of the frequency-doubled YAG (yttrium aluminum garnet)-type emitting, at a wavelength $\lambda_1$ equal to 532 nm for example, a pulsed beam 9 (see FIG. 3).

Figure 2:
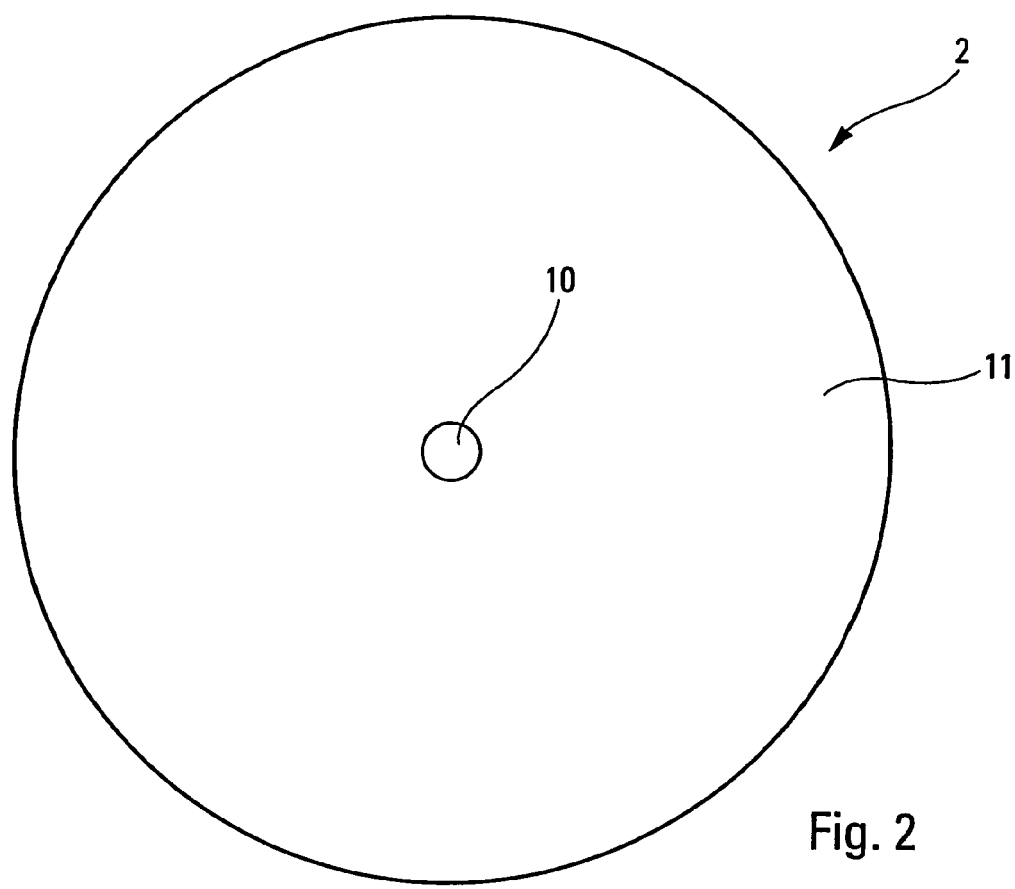
FIG. 2 is a very enlarged schematic cross section of the optical fiber used in the analyzer of FIG. 1.

The optical fiber 2 is of the monomode type with a specific wavelength. It comprises (see FIG. 2) a core 10, for example made of very pure silica, surrounded by a cladding 11, for example made of silica of lower quality. The diameter of the core 10 is between a few microns and at most about ten microns, whereas the diameter of the cladding 11 exceeds one hundred microns. In addition, the refractive index of the cladding 11 is lower than that of the core 10.

In general, the monomode optical fiber 2 is matched to the monomode transmission of a laser beam 9 of defined specific wavelength with, however, a few tolerances: thus, in the example given above of a laser beam 9 operating at 532 nm, it would be possible to use a commercially available monomode optical fiber 2 especially constructed for the monomode transmission of a laser beam of wavelength equal to 514 nm.

In the coupler 3, the pulsed coherent beam 9 is focused by an optic 12 onto the end face 10a of the core 10, corresponding to the end 2a of the fiber 2 (see FIG. 3).

Emerging at the opposite end 2b of the monomode optical fiber 2, from the core 10, is the light beam 13 that illuminates the particles 8.

It is absolutely essential for the laser 1 to deliver, at each pulse of the laser beam 9, a high energy so that each pulse of the light beam 13 illuminates said particles 8 sufficiently for the camera 6 to be able to form satisfactory images thereof.

For this purpose, the peak power of the laser beam 9 is chosen to be high enough for, on the one hand, the particles 8 to be correctly illuminated, so that the camera 6 can form their image, and, on the other hand, the spectrum of the illuminating light beam 13 to include, in addition to the wavelength of the laser beam 9, lines of shifted wavelengths generated by Raman conversion in the core 10 in order, according to the invention, to remove the background noise and the moiré effect from the images.

By reducing the length of the monomode optical fiber 2, the Raman lines in the infrared and close to the infrared, which are unnecessary and detrimental, are removed.

Moreover, to facilitate the injection, without saturation, of the high energy of the laser beam 9 into the end 10a of the core 10, the monomode fiber 2 having a specific wavelength is matched to a wavelength 2 greater than the wavelength $\lambda_1$ of the laser beam. Thus, the diameter of the core 10 is larger than if the monomode fiber 2 were strictly matched to the wavelength $\lambda_1$.

In the above example, in which $\lambda_1$ is equal to 532 nm, $\lambda_2$ may be chosen to be equal to 630 nm so that the $\lambda_2/\lambda_1$ ratio is approximately 1.2.

The invention claimed is:

1. A method for illuminating particles for the purpose of forming their images, in which method a coherent light beam is injected into the core of a monomode optical fiber at one end of said fiber, the other end of this optical fiber illuminates a field optic that focuses the light beam emerging from the optical fiber onto the objective optic of a camera, defining a measurement region in which said particles lie, and said particles are illuminated by the light beam emanating from said core for allowing the camera to form images thereof, wherein the peak power of said injected coherent light beam is chosen so that, on the one hand, the particles are correctly illuminated so that the camera can form their image, and, on the other hand, the spectrum of the illuminating light beam includes, in addition to the wavelength of the laser beam, lines of shifted wavelengths generated by Raman conversion in the core in order to remove the background noise and the moiré effect from the images.

2. The method as claimed in claim 1, wherein the Raman lines whose wavelength forms part of the infrared range and those whose wavelength is close to this range are removed from said spectrum.

3. The method as claimed in claim 2, wherein said Raman lines corresponding to the infrared or close to the infrared are removed by adjusting the length of said monomode optical fiber.

4. The method as claimed in claim 1, in the implementation of which a monomode optical fiber having a specific wavelength is used, that is to say a monomode optical fiber in which the diameter of the core is matched to the wavelength of the beam to be transmitted by the optical fiber and is an increasing function of said wavelength, wherein said coherent light beam, having a wavelength of $\lambda_1$, is injected into the core of a monomode optical fiber having a specific wavelength matched to a wavelength $\lambda_2$ of greater than $\lambda_1$.

5. The method as claimed in claim 4, wherein the $\lambda_2/\lambda_1$ ratio is at least approximately equal to 1.2.

6. The method as claimed in claim 4, wherein $\lambda_1$ is equal to 532 nm and $\lambda_2$ is equal to 630 nm.

* * * * *